United States Patent [19]

Leonard

[11] Patent Number: 5,512,458
[45] Date of Patent: Apr. 30, 1996

[54] METHOD OF USING MOBILE PRIMING SITES FOR DNA SEQUENCING

[75] Inventor: Jack T. Leonard, Somerville, Mass.

[73] Assignee: W. R. Grace & Co.-Conn., New York, N.Y.

[21] Appl. No.: 275,169

[22] Filed: Jul. 14, 1994

Related U.S. Application Data

[63] Continuation-in-part of Ser. No. 202,400, Feb. 25, 1994.

[51] Int. Cl.$^6$ .............................. C12P 19/34; C12Q 1/68; C07H 21/02; C07H 21/04
[52] U.S. Cl. .................... 435/91.1; 435/91.2; 435/6; 435/810; 536/23.1; 536/24.3
[58] Field of Search .................... 435/6, 91.1, 91.2, 435/810, 183; 536/23.1, 24.3; 935/9, 7, 8, 77, 78; 436/501, 546; 549/223, 227; 548/303.7; 252/645

[56] References Cited

U.S. PATENT DOCUMENTS 5,426,039  6/1995  Wallace et al. .................... 435/91.2

FOREIGN PATENT DOCUMENTS

| | | |
|---|---|---|
| 2036946 | 10/1991 | Canada . |
| 0224126 | 5/1987 | European Pat. Off. . |
| 221909 | 7/1989 | United Kingdom . |
| WO94/01582 | 1/1994 | WIPO . |

OTHER PUBLICATIONS

Friend, Tim, "High-tech labs shorten the path to new genes," *U.S.A. Today*, Mar. 22, 1994; p. 5D.
Lamerdin, Jane E. and Carrano, Anthony V., "Automated Fluorescence-Based Restriction Fragment Analysis," *BioTechniques*, vol. 15, No. 2 (1993); pp. 294–302.
Unrau, Paul and Deugau, Kenneth V., "Non-cloning amplification of specific DNA fragments from whole genomic DNA digests using DNA 'indexers'", *Gene*, 145(1994); pp. 163–169.
Vooijs, M., Yu, L. C., Tkachuk, D. Pinkel, D. Johsnon, D., Gray, J. W.; "Libraries for Each Human Chromosome, Construction From Sorter-enriched Chromosomes by Using Linker-Adaptor PCR", Am. J. Hum. Genet., 52:586–597, 1993.
Wesley, Cedric S., Ben, Mathew, Martin, Krietman, Hagag, Nabil, Eanes, Walter F., "Cloning regions of the drosophila genome by microdissection of polytene chromosome DNA and PCR with nonspecific primer", *Nucleic Acids Research*, vol. 18, No. 3; pp. 599–603.

*Primary Examiner*—W. Gary Jones
*Assistant Examiner*—Bradley L. Sisson
*Attorney, Agent, or Firm*—Nicholas P. Triano, III; William L. Baker

[57] ABSTRACT

Doubled-stranded oligonucleotide molecules for use in providing enchaned sequencing of DNA, comprising: a first stand having 1) a priming site; 2) a labeling region contiguous with the priming site, wherein the labeling region consists essentially of at least six identical nucleotides; and 3) a cohesive end contiguous with the labeling region, having a nucleotide sequence complementary to a nucleotide sequence generated by the action of a restriction enzyme; and a second strand annealed to the labeling region of the first stand, but not overlapping with the cohesive end. A method of DNA gene sequencing, involving the use of mobile priming sites for DNA polymerases in DNA sequencing, is also disclosed.

39 Claims, No Drawings

METHOD OF USING MOBILE PRIMING SITES FOR DNA SEQUENCING

This application is a continuation-in-part of pending U.S. application Ser. No. 08/202,400, filed Feb. 25, 1994, the disclosure of which is incorporated herein by reference.

FIELD OF THE INVENTION

This invention relates to improvements in DNA characterization involving the use of mobile DNA priming sites for DNA sequencing.

BACKGROUND OF THE INVENTION

The desired end-product of most DNA characterization procedures is the nucleotide sequence of the DNA. The laboratory procedures which commonly precede DNA sequencing are 1) restriction mapping, and 2) subcloning or polymerase chain reaction ("PCR") amplification. The function of subcloning is to is divide large DNA fragments into smaller fragments which can be propagated in a suitable host, thereby providing large amounts of template, i.e., the DNA segments or fragments of interest that are being cloned for sequencing. The subcloning procedure also provides primer sites carried on the vector DNA which may be used in DNA sequencing.

DNA sequencing and PCR rely on the ability of a DNA polymerase to extend an oligonucleotide primer that is annealed to a single stranded DNA template. During thermal cycle DNA sequencing, a thermostable DNA polymerase is used with a single oligonucleotide primer. PCR ordinarily extends primers from two complementary DNA strands, and thus makes double stranded DNA product, whereas asymmetric PCR produces predominantly single-stranded DNA by limiting the concentration of one primer while adding an excess of another.

For the DNA sequencing and PCR methods described above to succeed, the primer(s) must be complementary to the primer site(s) on the template DNA, i.e., the primer site on the template DNA and the oligonucleotide primer must be closely matched to ensure that annealing takes place at the desired location. Since the potential priming sites are known on vector DNA (and on the ends of PCR product), sequencing can be carried out directly on this DNA; however, due to practical limitations of sequencing technology, DNA may only be sequenced from the priming site to a maximum length of about 300 nucleotides ("nt"). If the DNA sequence on the ends of restriction fragments were known, complementary primers thereto could be synthesized, and the DNA sequenced. However, when uncharacterized DNA is restriction mapped, only a remnant of the nucleotide sequence generated by the action of the endonucleases (typically 2–4nt), is known. The length of this cleavage site is inadequate to design a primer for DNA sequencing or PCR amplification.

Another problem inherent in current sequencing technology is as follows. Because restriction mapping is a "top-to-bottom approach" where large fragments are progressively reduced to equimolar amounts of smaller fragments, those smaller fragments become increasingly more difficult to detect and manipulate. In the past, this limitation was remedied by cloning into small multicopy plasmids, and transforming laboratory strains of easily propagated and genetically well-characterized hosts. However, plasmid rearrangement, insert size limitation, possible dissemination of antibiotic resistance, containment of recombinant organisms, and "unclonable" fragments, are just a small sampling of the problems associated with maintaining and propagating of DNA in living organisms. Another limitation of current DNA methods is that most restriction fragments are refractory to nucleotide sequencing techniques, because the minimum sequence information necessary to design an oligonucleotide primer is unavailable. Furthermore, when subcloning is used, the total procedure (if successful) takes at least 80 hours total elapsed time and many steps; it would obviously be a great advantage to reduce this time. As such, improvements in the ease of sequencing DNA that address these problems have long been desired.

Yet another limitation of currently practiced DNA sequencing techniques is the throughput limitation imposed by the sensitivity of detection of sequencing cloning products by, most notably, autoradiography. In conventional manual sequencing protocols, for example, the products of cloning, the DNA fragment(s) of interest having a known priming site sequence at one end, are 1 ) labeled and 2) terminated. In the labeling step, one takes the products of cloning and labels them using DNA polymerase. The mix in which the reaction takes place contains one radioactive (generally, either $^{35}$S-, $^{32}$p- or $^{33}$p- labeled) deoxynucleotide triphosphates ("dNTPs"), as well as non-radioactive dNTPs. The enzyme will incorporate the radioactive nucleotide(s) into the DNA fragments so the fragments are visible via autoradiography. The ease with which sequencing product is detected is proportional to the amount of label which is incorporated during the labeling step. One dNTP is deliberately left out of the labeling mixture. This controls the length of the labeled primer in the labeling step. This process is generally repeated about 60X in thermal cycle sequencing protocols.

In the termination step, the labeled, extended primer is added to the just prepared termination mixes. In manual sequencing protocols, there are four separate termination mixes into which the labeling reaction is divided. All have one of four different dNTP analogs present (either dideoxy-GTP, dideoxy-ATP, dideoxy-TTP, or dideoxy-CTP) in addition to the four normal dNTP's. The analogs are incorporated into the growing DNA strand by polymerase at low frequency, but once this has been done, the DNA strand can not be extended any further. The ratio of normal dNTP's to analogs (dideoxynucleotide triphosphates ("ddNTPs")) is adjusted so that ddNTP is only incorporated occasionally leading Is to sequencing products of many different lengths, but all terminating in the same ddNTP. The four termination mixtures (i.e., ddGTP, ddATP, ddTTP, and ddCTP) are electrophoresed side-by-side in polyacrylamide. The resultant DNA sequencing ladder is detected by autoradiography, whereupon analysis of the image will elucidate the DNA sequence.

One can see that the sensitivity of detection is determined by the amount of template DNA utilized, and the duration of the autoradiography. These limitations may be seen as an impediment to high throughput DNA sequencing. In conventional DNA sequencing, as described above, priming sites are selected from vector sequences which are adjacent to insert DNA. The number of s radioactive nucleotides incorporated (sensitivity) is controlled by priming site selection. Naturally-occurring priming sites rarely allow the incorporation of more than 4 or 5 radioactive nucleotides using the labeling method described above. As such, if the autoradiographic image corresponding to the banding pattern in the polyacrylamide gel is too faint, another film must be exposed, resulting in a delay in obtaining sequencing information equal to the time necessary to expose and develop the film, which can be up to 72 hours in some cases. Improvements in the sensitivity of autoradiographic detection, and therefore, faster sequencing, have been sought out.

SUMMARY OF THE INVENTION

This invention relates to double-stranded oligonucleotide molecules for use in providing enhanced sequencing of DNA, comprising: a first strand having 1) a priming site; 2) a labeling region contiguous with the priming site; and 3) a cohesive end contiguous with the labeling region, having a nucleotide sequence complementary to a nucleotide sequence generated by the action of a restriction enzyme; and a second complementary strand annealed to the labeling region of the first strand, but not overlapping with the cohesive end.

The invention further relates to a method of sequencing DNA, comprising a) subjecting DNA to the action of more than one restriction enzyme so as to prepare a restriction digest, the action resulting in restriction fragments having at least one sticky end; b) forming activated DNA segments by ligating to the restriction fragments a double-stranded oligonucleotide molecule comprising: a first strand having a priming site, a labeling region contiguous with the priming site, and a cohesive end contiguous with the labeling region, the cohesive end having a nucleotide sequence complementary to the nucleotide sequence of the sticky end, wherein the double-stranded oligonucleotide molecule has been tagged with a light-responsive dye having a photometric response unique to that particular double-stranded oligonucleotide molecule; c) separating the activated DNA segments, and d) directly sequencing the activated DNA segments.

The invention further relates to a method of sequencing DNA, comprising the steps of a) identifying on a DNA molecule a segment containing genetic information of interest; b)selecting a restriction enzyme that will excise the segment and leave at least one end of the segment with a sticky end; c) making a restriction digest by treating the DNA molecule with the restriction enzyme, excising the segment and leaving at least one end of the segment with a sticky end; d) selecting a prinker comprising a double-stranded oligonucleotide molecule for use in providing enhanced sequencing of DNA, comprising a first s strand having 1 ) a priming site; 2) a labeling region contiguous with the priming site; and 3) a cohesive end contiguous with the labeling region, the cohesive end having a nucleotide sequence complementary to the sticky end of the segment; and a second strand annealed to the labeling region of the first strand, but not overlapping with the cohesive end; e) ligating the prinker to the segment to form an activated DNA segment; f) isolating the activated DNA segments from the restriction digest; and g) directly sequencing the activated DNA segments.

DESCRIPTION OF THE INVENTION

The invention describes a method by which "sticky ended" restriction fragments are ligated to double stranded DNA oligonucleotides of known sequence (i.e., linkers) having a sticky end complementary to that on the restriction fragments, with the resulting "activated" DNA molecules isolated and subjected to DNA sequencing. One strand of the linker provides the priming site for DNA sequencing. It is proposed that this class of specialized oligonucleotides be termed "prinkers," to indicate the combination of priming and linking functions. "Primer" is used herein in accordance with its generally accepted definition: (single-stranded) oligonucleotides which will anneal to complementary priming sites by virtue of specific hydrogen-bonding interactions, and, in particular, oligonucleotides which are used to anneal to target sequences, i.e., DNA polymerase priming sites. "Linker" is also used herein in accordance with its generally accepted definition: double-stranded DNA "adapters" which are ligated onto the end of restriction fragments. After a prinker has been ligated to a target DNA segment containing genetic information of interest, the segment is now what may be called, for present purposes, "activated" and may be easily sequenced directly. The activated DNA segment can be sequenced directly once it has been isolated from the rest of the restriction digest (e.g., by gel electrophoresis). If there is not a sufficient amount of the is activated DNA segment available for direct DNA sequencing, the sequencing products can be amplified by thermal cycle sequencing ("TCS"). Alternatively, the PCR can be carried out on the activated DNA segment using primers complementary to the prinkers prior to DNA sequencing. This may be done by amplifying the purified activated segment or the whole digest to increase the amount of the desired segment.

Prinkers in accordance with the invention have the following general design features:

| Upper Strand: 5'[ | Complementary Strand] 3' |
| Lower Strand: 3'[ Priming Site] - [Labeling Region] - [Cohesive End] 5' |

Priming Site: Optimal target for annealing primer prior to treatment with polymerase; defines the primer sequence.

Labeling Region: Template sequence which directs DNA polymerase to incorporate multiple labeled, e.g., radioactive, nucleotides. The Labeling Region comprises from at least four to thirty identical nucleotides, preferably from four to ten identical nucleotides, more preferably six to ten identical nucleotides, and even more preferably eight to ten identical nucleotides.

Cohesive End: Provides compatible ends for ligation of prinkers to restriction fragments.

Complementary Strand: Provides a region of double-stranded DNA which is required by DNA ligases for the attachment of prinker to restriction fragment. The end of this strand proximate to the Cohesive End approaches, but does not overlap, the Cohesive End; the end of this strand proximate to the Priming Site preferably extends to the end of the Priming Site, although in some cases the Priming Site may be left "bare".

A specific example of a prinker in accordance with this general model is shown below:

```
                 * * * * * * * * * * * * * * * * * *    * * * * * *    * * * * * *
                                                        Complementary Strand
5'                                                      AACAAAAAACAAAAAATG        3'
3'-GGGGGTGGAGGACGGGTATTTTTTTTTTTTTTTTTTGTTTTTTGTTTTTTACTTAA-5'
 |      Priming Site      |       Labeling region                   |  Cohesive end |
```

\*-Positions where labeled dATPs can be incorporated by DNA polymerase.
 -Position at which DNA polymerase will pause if dTTP is withheld from the labeling reaction.
The polymerase will resume synthesis from this point when the labeling mixture is divided into the four termination mixtures (as discussed hereinbelow).

As can be seen from the specific example above, the design of the prinker allows for the incorporation of much more labeled nucleotide when the DNA fragments of interest are treated with DNA polymerase in the labeling step, e.g., in preparation for autoradiography. As such, even small quantities of extended primer will be detected when the image of the electrophoresis gel is developed, resulting in tremendous savings in time and money. Furthermore, the invention need not be limited to the use of radioactively-labeled nucleotides, as will be discussed below; nucleotides having other markers attached, such as biotin or s fluorescein, may be used as well when it is desired to visualize the bands on the gel using, e.g., strept-avidin, photometric or fluorescence detection.

A particularly advantageous embodiment of the invention involves the use of prinkers in sequencing DNA which has been multiply-digested with different restriction enzymes. Treating DNA of interest with different restriction enzymes will result in the production of many restriction fragments having the characteristic sticky end of the enzyme that cleaved the DNA. Identifying, isolating and sequencing the restriction fragments produced by the action of a specific set of enzymes in the mix would be highly impracticable with current technology. The sequencing of the individual products of such a multiple restriction digest would involve time-consuming subcloning, etc., the drawbacks of which have been discussed above. However, through the use of prinkers, each having a unique label or tag (e.g., a light-responsive dye; "light-responsive" is meant to refer to dyes which have a characteristic response to light such as absorption or fluorescence) and a sticky end complementary to a sticky end produced by a restriction enzyme in the mix, all the fragments produced by a particular combination of restriction enzymes may be identified and sequenced quite easily. For example, four different prinkers as described above, having sticky ends characteristic of those made through the enzymatic action of BamH I, Pst I, EcoR I and Hind III on DNA could be produced with each having a different light-responsive marker (e.g., fluorochromes) attached. Each prinker may be tagged or derivatized with the light-responsive marker, i.e., at the 3' end of one of the prinker's strands, or the prinker may be internally labeled with nucleotides carrying the light-responsive marker. Each light-responsive marker should be photometrically distinct. DNA of interest would then be multiply-digested, and the differentially-labeled prinkers described above are added to the mix and ligated to the fragments in a target-specific fashion. The ligated fragments would then be separated by electrophoresis, and visualized. The resulting image would allow identification of each fragment by the unique photometric response of each marker, allowing the researcher to determine the size and origin of each fragment. After analysis of the electrophoresis data is complete, each band may then be isolated from the gel using known techniques, and sequenced directly as discussed above.

The use of prinkers as described above may be used to advantageously provide automated restriction mapping. Prinkers (or other DNA providing cohesive ends, e.g., linkers) are provided which allow internal labeling with different fluorescent dyes. These are then ligated to very small amounts of multiply-digested cosmid, plasmid or BAC DNA, thus permitting automated s restriction mapping of large DNA's with a minimum of material. Different dyes will be targeted to certain cleavage products of endonucleases by the prinker to which the dyes were linked. The ends of cleavage products can then be readily identified by this method using a suitable detector.

The construction of a restriction map using four endonucleases, for example, would require fifteen separate restriction digests which would include all possible single (n=4), double (n=6), triple (n=4), and quadruple (n=1) digests, followed by ligation to four differentially labeled prinkers. Fragments between 100 and 1000 base pairs could be detected on a single polyacrylamide gel using existing equipment (e.g., the ABI Model 373A DNA Sequencer). Other separation techniques such as capillary electrophoresis (CE), high performance liquid chromatography (HPLC), or agarose gel electrophoresis could be used to increase the resolution of a wider range of restriction fragments. The signal intensity of the fluorescently labeled restriction fragments ought to be independent of fragment size or the number of fragments generated. Abnormal signal intensities would indicate that more than one band was running at the same position. Two different dyes detected on the same fragment would indicate different ends. Computer software would be needed to assemble restriction s maps from the identified fragments, and suitably designed software could also provide a rational DNA sequencing strategy. Purification of the fluorescently-labeled restriction fragments could be conducted with the automated restriction mapping procedure described above. A fraction collector could be positioned just downstream of the signal detector to separate the labeled restriction fragments as they emerge from an analytical device. If it is found that there is inadequate amount of template for a direct sequencing approach (i.e., requiring amplification), then isolated products from the mapping experiments above could be amplified using known techniques, purified and sequenced. Dyes covalently-linked to the template strand will not co-migrate with the sequencing is product, and therefore would not interfere with dye labeled primer-based or DyeDeoxy™ (Applied Biosystems) terminator-based sequencing. Alternately, thermal cycle sequencing could be conducted on purified fragments using a radioisotopic approach, because this technique would allow the researcher to sequence limited quantities of purified DNA.

By reference to Table I, which details Type II endonuclease sequences, it can be seen that a library of prinkers having sticky ends complementary to the characteristic nucleotide overhang sequences of all known endonucleases is within the scope of the invention. By assembling a library of prinkers, all having known priming sites, but each having one of the sequences listed in Table I, a kit for sequencing DNA in accordance with the invention may be obtained. One of ordinary skill in the art can easily see that having the kit at hand, DNA sequencing in accordance with the invention of any desired sequence may be accomplished because no matter what restriction enzyme is used in the restriction digest, there will be a prinker in the kit that may be ligated to the fragment(s) of interest.

Many Type II endonucleases produce specific single stranded overhangs, either two or four nucleotides in length. These overhangs, known as "sticky ends", can be ligated to the complementary ends of another DNA molecule, using T4 DNA ligase. Different DNA fragments that can be ligated together by virtue of their sticky ends are said to possess compatible cohesive ends. Other endonucleases either generate "blunt ends" or a variety of sticky ends. These would be of limited use because blunt ends ligate poorly, and unknown sticky ends can not be specifically targeted for ligation. As such, sticky ends identical to Type II endonuclease cleavage products, shown in Table I, are preferred.

(carrying a defined priming site) to the ends of a restriction fragment, which could then be amplified if necessary, before isolation and sequencing. The resultant product(s) could be isolated and restricted again. This process could be repeated indefinitely, circumventing subcloning procedures altogether. The identity of restriction sites on the ends of restriction fragments from multiple restriction digests could be identified using different combinations of prinkers, followed by ligation and amplification. Alternately, prinkers could be internally labeled or tagged with dyes, which could be used to identify restriction sites after ligation of such differentially-labeled prinkers to restriction fragments, with subsequent sequencing of the DNA. Restriction sites encoded on the prinkers could facilitate their cloning if desired.

The attachment of prinkers to restriction fragments defines the ends and immediately makes them accessible to sequencing primers. The ligation of different prinkers to

TABLE I

PRINKER OVERHANGS AND COMPATIBILITY WITH RESTRICTION FRAGMENTS

| | Prinker overhang | Compatible with restriction fragments generated by (isoschizomers not listed) |
|---|---|---|
| 1 | 5'-AATT: | Tsp509 I, Apo I, Mun I, EcoR I |
| 2 | 5'-CG: | Mae II, Psp1406 I, BsaH I, Hpa II, HinP I, Nar I, Tag I, Cla I, Acc I*, BstB I, Aci I |
| 3 | ACGT-3': | Aat II |
| 4 | 5'-AGCT: | Hind III |
| 5 | AGCT-3': | Sac 1, Ban II, BsiHKA I, Bsp1286 I |
| 6 | 5'-TA: | Nde I, Bfa I, Csp6 I, Mse I, Ase I |
| 7 | 5'-CATG: | Afl III, Nco I, Sty I, Dsa I, BspH I |
| 8 | CATG-3': | Nla III, NspH I, Sph I |
| 9 | 5'-CCGG: | Age I, BsrF I, BsaW I, Xma I, Ava I, NgoM I, BspE I |
| 10 | 5'-CGCG: | Asc I, Mlu I, Afl III, Dsa I, BssH II |
| 11 | 5'-CTAG: | Spe I, Avr II, Sty I, Nhe I, Xba I |
| 12 | 5'-GATC: | Mbo I, Bgl II, BstY I, BamH I, Bcl I |
| 13 | AT-3': | Pvu I, BsiE I |
| 14 | CG-3': | Hha I |
| 15 | 5'-GCGC: | Kas I, Ban I |
| 16 | GCGC-3': | Hae II, Bbe I |
| 17 | 5'-GGCC: | Not I, Eag I, Eae I, Gdi II, Bsp120 I |
| 18 | GC-3': | BsiE I, Sac II |
| 19 | GGCC-3': | Apa I, Ban II, Bsp1286 I |
| 20 | 5'-GTAC: | BsiW I, Acc65 I, Ban I, BsrG I |
| 21 | GTAC-3': | Kpn I |
| 22 | 5'-TATA: | Sfc I |
| 23 | 5'-AT: | Acc I |
| 24 | 5'-TCGA: | Xho I, Ava I, Sal I |
| 25 | 5'-TGCA: | Ppu10 I, Sfc I, ApaL I |
| 26 | TGCA-3': | Sse8387 I, Nsi I, Pst I, Bsp1286 I, BsiHKA I |
| 27 | 5'-TTAA: | Afl II |

*Restriction fragments generated by restriction enzymes in bold may require the use of more than one type of prinker because of degeneracy in the recognition site.

It can be seen that although the recognition sequences of the endonucleases Mbo I, Bgl II, BamH I, and Bcl I are different, they all generate the same four nucleotide single stranded 5' overhang (5'-GATC) when they cleave DNA. As a result, one prinker with a compatible cohesive end (i.e., 5'-GATC) could be ligated to the cleavage products of all the four endonucleases listed above. Thus, a complete set of prinkers that has compatible cohesive ends with the cleavage products of all useful endonucleases would be considerably smaller in number than the endonucleases that generate those products.

The use of the invention would obviate the problems associated with maintenance and propagation of DNA in organisms and allow for the generation of large amounts of virtually any restriction fragment, by attaching a prinker, either end of the same restriction fragment would allow the fragment to be sequenced from both ends. Alternatively, a fragment with the same prinker on both ends could be restricted with a different endonuclease s which cuts internally to the restriction fragment, separated by conventional techniques, and the fragments sequenced separately. If sequencing was required from both ends of the two fragments, a separate prinker could be ligated to the cleavage site prior to separation of the two fragments.

DNA template preparation is a major technical barrier to rapid de novo and diagnostic DNA sequencing. This invention allows the integration of analytical and preparative techniques upstream of DNA sequencing, thereby increasing the rate of DNA characterization by at least one order of magnitude. Prinkers, labeled or tagged with different light-responsive dyes, can be joined to the products of certain endonucleases in a target-specific manner using DNA ligase. The separation of the activated fragments during the process of automated restriction analysis can also serve to purify DNA template. Thus, prinkers may replace subcloning as the predominant method of DNA template preparation prior to DNA sequencing.

A surprising advantage of the invention is, because the sequence of the mobile priming site carried on the prinker is known, the amplification conditions s for PCR may be optimized, e.g., for yield or specificity. This in turn simplifies sequencing. For example, if the proper experimental conditions are available for the use of a thermal stable DNA polymerase, a prinker containing a priming site designed for optimum use with that enzyme may be employed in the procedure. Another advantage is that it is easier and more efficient to incorporate radioactive nucleotides during sequencing; because the primer nucleotide sequence is known, one knows exactly which radioactive nucleotides to incorporate into the polymerase mixture. Reference may be made to the Example for another surprising benefit of the invention, the reduction of time required for sequencing using the invention, in comparison to the subcloning procedure.

Another embodiment of the invention may be found where the restriction fragments generated by an endonuclease are sufficiently abundant to sequence without amplification. In this case, one may choose to alkaline phosphatase the restriction fragments before ligating them to the appropriate prinkers. The alkaline phosphatase removes the 5'-terminal phosphate from the restriction fragment; thus, when the prinker is attached to the restriction fragment, only one of the two complementary oligonucleotide strands (the phosphorylated strand) of the prinker is ligated to the restriction fragment. The ligated oligonucleotide then serves as a "naked" priming site during DNA sequencing. The priming site is "naked" in the sense that ordinarily the primer must compete with one of the two strands of the double stranded DNA template for the priming site, which necessitates denaturation steps. Since the top strand of the prinker, which occupies the priming site, is not covalently attached to the restriction fragment, it can serve as the primer.

Alternately, an excess of shorter primer can be annealed to its complementary priming site and the intervening sequence (i.e., labeling region) between the priming site and complementary cohesive end can be used to label primer extensions to high specific activity and thereby enhance detection of DNA sequencing product.

EXAMPLE

A comparison of the time requirements for sequencing a DNA segment of interest was made between a procedure practiced in accordance with the invention and a subcloning procedure. The steps used for carrying out both procedures are seen in Tables II and III, below; those of ordinary skill in the art will understand how to carry out the procedure for each step. The inventive procedure cuts in half both the total time required for sequencing (now 26–30 hours) and the number of procedural steps (now 12), compared to the subcloning procedure, with the same or better results obtained.

TABLE II

SEQUENCING PROCEDURE USING INVENTION

| Step | Procedure | Time | Purpose |
|---|---|---|---|
| 1 | Restriction Digest | 1 hr | Generation of restriction fragments |
| 2 | Deproteinization or enzyme inactivation | 5 min | Enzyme removal/inactivation |
| 3 | Centrifugal ultrafiltration with MICROCON ™-100 † | 30 min | Buffer exchange |
| 4 | Ligation | 1–4 hr | Ligation of prinkers to restriction fragments |
| 5 | Preparative electrophoresis | 1.5 hr | Separation of prinker-attached restriction fragments |
| 6 | β-agarase treatment or centrifugal ultrafiltration with MICROPURE ™† | 5 min- 1 hr | Purification of prinker-attached restriction fragments |
| 7 | Centrifugal ultrafiltration with MICROCON ™-100 | 45 min | Concentration and buffer exchange |
| 8 | Sequencing | 2 hr | Generation of sequencing product |
| 9 | Electrophoresis | 2 hr | Separation of sequencing products |
| 10 | Dry electrophoresis gel | 1 hr | |
| 11 | Autoradiography | 8 hr | Exposure of X-ray film to sequencing product |
| 12 | Develop film | 20 min | Detect signal on film |

†Amicon, Inc. (Beverly, Massachusetts)

TABLE III

SEQUENCING PROCEDURE USING SUBCLONING

| Step | Procedure | Time | Comments |
|---|---|---|---|
| 1 | Restriction Digest | 1 hr | |
| 2 | Preparative Electrophoresis | 1.5 hr | |
| 3 | β-agarase treatment or centrifugal ultrafiltration with MICROPURE ™ | 5 min- 1 hr | |
| 4 | Centrifugal ultrafiltration with MICROCON ™-100 or precipitate | 45 min | |
| 5 | Ligation | 4–16 hr | |
| 6 | Transformation | 1 hr | |
| 7 | Plating on agar | 5 min | |
| 8 | Growth of bacterial colonies | 17–19 hr | If no transformants, repeat from step 1 |

TABLE III-continued

SEQUENCING PROCEDURE USING SUBCLONING

| Step | Procedure | Time | Comments |
|---|---|---|---|
| 9 | Pick colonies/Growth in broth | 20 hr | |
| 10 | Pellet bacteria | 15 min | |
| 11 | Resuspend in buffer; transfer to centrifuge tubes | 2 min | |
| 12 | Add lysis buffer | 15 min | |
| 13 | Add neutralization buffer | 15 min | |
| 14 | Precipitate DNA | 1 hr | |
| 15 | Resuspend, wash and re-precipitate | 30 min–1 hr | |
| 16 | Screen for inserts (restriction digests) | 1 hr | |
| 17 | Analytical electrophoresis | 1.5 hr | If no inserts or wrong inserts, repeat from step 1 |
| 18 | Denature plasmid and anneal primer | 30 min | |
| 19 | Sequencing | 2 hr | |
| 20 | Electrophoresis | 2 hr | |
| 21 | Dry electrophoresis gel | 1 hr | |
| 22 | Autoradiography | 24 hr | |
| 23 | Develop film | 20 min | |

4. The double-stranded oligonucleotide molecule of claim 1 wherein said labeling region consists essentially of from at least six to ten identical nucleotides.

5. The double-stranded oligonucleotide molecule of claim 1 wherein said labeling region consists essentially of from at least eight to ten identical nucleotides.

6. The double-stranded oligonucleotide molecule of claim 1 wherein the nucleotide sequence of said cohesive end is complementary to the nucleotide sequence generated by the action of a Type II endonuclease on DNA.

7. The double-stranded oligonucleotide molecule of claim 6 wherein the nucleotide sequence of said cohesive end is selected from the group consisting of 5'-AATT; 5'-CG; ACGT-3'; 5'-AGCT; AGCT-3'; 5'-TA; 5'-CATG; CATG-3'; 5'-CCGG; 5'-CGCG; 5'-CTAG; 5'-GATC; AT-3'; CG-3'; 5'-GCGC; GCGC-3'; 5'-GGCC; GC-3'; GGCC-3'; 5'-GTAC; GTAC-3'; 5'-TATA; 5'-TCGA: 5'-TGCA; TGCA-3'; and 5'-TTAA.

8. The double-stranded oligonucleotide molecule of claim 1 further comprising a chemical marker covalently bonded to one of said strands.

9. The double-stranded oligonucleotide molecule of claim 8, wherein said chemical marker is selected from the group consisting of biotin and the fluorochromes.

10. The double-stranded oligonucleotide molecule of claim 8, wherein said chemical marker is fluorescein.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 56 bases
        ( B ) TYPE: nucleic acid
        ( C ) STRANDEDNESS: double
        ( D ) TOPOLOGY: linear ( i i i ) HYPOTHETICAL: Yes ( x i ) SEQUENCE DESCRIPTION: SEQ ID NO: 1:

```
                                                  AACAAA  AAACAAAAAA  TG
GGGGGTGGAG  GACGGGTATT  TTTTTTTTT  TTTTTGTTT  TTTGTTTTT  ACTTAA  5 6
```

---

What is claimed is:

1. A double-stranded oligonucleotide molecule for use in providing enhanced sequencing of DNA, comprising:

a first strand having 1) a priming site; 2) a labeling region contiguous with said priming site; and 3) a cohesive end contiguous with said labeling region, said cohesive end having a nucleotide sequence complementary to a nucleotide sequence generated by the action of a restriction enzyme; and a second strand annealed to said labeling region of said first strand, but not overlapping with said cohesive end.

2. The double-stranded oligonucleotide molecule of claim 1 wherein said labeling region consists essentially of from at least four to thirty identical nucleotides.

3. The double-stranded oligonucleotide molecule of claim 1 wherein said labeling region consists essentially of from at least four to ten identical nucleotides.

11. A kit for sequencing selected restriction fragments comprising a library of prinkers, each of said prinkers comprising a double-stranded oligonucleotide portion having a first strand having 1) a priming site; 2) a labeling region contiguous with said priming site, said labeling region consisting essentially of at least six identical nucleotides; and 3) a cohesive end contiguous with said labeling region, said cohesive end having a nucleotide sequence selected from the group consisting of 5'-AATT, 5'-CG, ACGT-3', 5'-AGCT, AGCT-3', 5'-TA, 5'-CATG, CATG-3', 5'-CCGG, 5'-CGCG, 5'-CTAG, 5'-GATC, AT-3', CG-3', 5'-GCGC, GCGC-3', 5'-GGCC, GC-3', GGCC-3', 5'-GTAC, GTAC-3', 5'-TATA, 5'-AT, 5'-TCGA, 5'-TGCA, TGCA-3', and 5'-TTAA; and a second strand annealed to said labeling region of said first strand, but not overlapping with said cohesive end.

12. A method of sequencing DNA, comprising the steps of a identifying on a DNA molecule a segment containing genetic information of interest;

b. selecting a restriction enzyme that will excise said segment and leave at least one end of said segment with a sticky end;

c. making a restriction digest by treating said DNA molecule with said restriction enzyme, excising said segment and leaving at least one end of said segment with a sticky end;

d. selecting a prinker comprising a double-stranded oligonucleotide molecule for use in providing enhanced sequencing of DNA, comprising:
   a first strand having 1) a priming site; 2) a labeling region contiguous 30 with said priming site; and 3) a cohesive end contiguous with said
   labeling region, said cohesive end having a nucleotide sequence complementary to said sticky end of said segment; and
   a second strand annealed to said labeling region of said first strand, but not overlapping with said cohesive end;

e. ligating said prinker to said segment to form an activated DNA segment;

f. isolating said activated DNA segments from said restriction digest;

g. directly sequencing some or all of said activated DNA segments.

13. The method of claim 12 wherein said sticky end is complementary to the nucleotide sequence generated by the action of a Type II endonuclease on DNA.

14. The method of claim 13 wherein said nucleotide sequence of said single-stranded sticky end of said prinker is selected from the group consisting of 5'-AATT; 5'-CG; ACGT-3'; 5'-AGCT; AGCT-3'; 5'-TA; 5'-CATG; CATG-3'; 5'-CCGG; 5'-CGCG; 5'-CTAG; 5'-GATC; AT-3'; CG-3'; 5'-GCGC; GCGC-3'; 5'-GGCC; GC-3'; GGCC-3'; 5'-GTAC; GTAC-3'; 5'-TATA; 5'-AT; 5'-TCGA; 5'-TGCA; 5'-TGCA; TGCA-3'; and 5'-TTAA.

15. The method of claim 12 further comprising the steps of amplifying said activated DNA segment to form a plurality of activated DNA segments before said isolation.

16. The method of claim 12 wherein said segment comprises two sticky ends.

17. The method of claim 16 wherein said activated DNA segment is sequenced from both ends.

18. The method of claim 16 further comprising the steps of cutting said activated DNA segment internally with a second restriction enzyme, to form two smaller activated DNA fragments, separating said smaller activated DNA fragments, and sequencing said fragments individually.

19. The method of claim 12 further comprising the step of removing the 5'-terminal phosphate group from said segment before ligating said prinker to said segment.

20. The method of claim 12 wherein said sequencing step comprises the steps of 1) amplifying said activated DNA segments using DNA polymerase in a mix containing radioactive nucleotides complementary to the nucleotides in said labeling region; 2) preparing termination mixtures, and 3) electrophoresing the products of said termination mixtures to provide a DNA sequencing ladder.

21. The method of claim 20 wherein said radioactive nucleotides are selected from the group containing $^{35}$S-, $^{32}$p- or $^{33}$p- labeled nucleotides.

22. The method of claim 12 wherein said labeling region consists essentially of from at least four to thirty identical nucleotides.

23. The method of claim 12 wherein said labeling region consists essentially of from at least four to ten identical nucleotides.

24. The method of claim 12 wherein said labeling region consists essentially of from at least six to ten identical nucleotides.

25. The method of claim 12 wherein said labeling region consists essentially of from at least eight to ten identical nucleotides.

26. A method of sequencing DNA, comprising
   a) subjecting DNA to the action of more than one restriction enzyme so as to prepare a restriction digest, said action resulting in restriction fragments having at least one sticky end;
   b) forming activated DNA segments by ligating to said restriction fragments a double-stranded oligonucleotide molecule comprising a first strand having a priming site, a labeling region contiguous with said priming site, and a cohesive end contiguous with said labeling region, said cohesive end having a nucleotide sequence complementary to the nucleotide sequence of said sticky end, wherein the double-stranded oligonucleotide molecule has been tagged with a light-responsive dye having a photometric response unique to that particular double-stranded oligonucleotide molecule;
   c) separating said activated DNA segments, and
   d) directly sequencing some or all of said activated DNA segments.

27. The method of claim 26 wherein said double-stranded oligonucleotide molecule is labeled before said activated DNA segments are formed.

28. The method of claim 26 wherein said sticky end is complementary to the nucleotide sequence generated by the action of a Type II endonuclease on DNA.

29. The method of claim 28 wherein said nucleotide sequence of said single-stranded sticky end of said prinker is selected from the group consisting of 5'-AATT; 5'-CG; ACGT-3'; 5'-AGCT; AGCT-3'; 5'-TA; 5'-CATG; CATG-3'; 5'-CCGG; 5'-CGCG; 5'-CTAG; 5'-GATC; AT-3'; CG-3'; 5'-GCGC; GCGC-3'; 5'-GGCC; GC-3'; GGCC-3'; 5'-GTAC; GTAC-3'; 5'-TATA; 5'-AT; 5'-TCGA; 5'-TGCA; TGCA-3'; and 5'-TTAA.

30. The method of claim 26 further comprising the steps of amplifying said activated DNA segment to form a plurality of activated DNA segments before said isolation.

31. The method of claim 26 wherein said fragments comprise two sticky ends.

32. The method of claim 31 wherein said activated DNA segment is sequenced from both ends.

33. The method of claim 28 wherein said light-responsive dye is selected from the group consisting of fluorochromes.

34. The method of claim 26 wherein said separation is accomplished by electrophoresis or liquid chromatography.

35. The method of claim 26 further comprising the step of preparing a restriction map before said sequencing step.

36. The method of claim 26 wherein said labeling region consists essentially of from at least four to thirty identical nucleotides.

37. The method of claim 26 wherein said labeling region consists essentially of from at least four to ten identical nucleotides.

38. The method of claim 26 wherein said labeling region consists essentially of from at least six to ten identical nucleotides.

39. The method of claim 26 wherein said labeling region consists essentially of from at least eight to ten identical nucleotides.

* * * * *